(12) United States Patent
Rehman et al.

(10) Patent No.: US 7,938,794 B2
(45) Date of Patent: May 10, 2011

(54) AIRWAY SUCTION SPOON

(75) Inventors: Jeff Rehman, Westminster, CO (US); Samuel David Say, Los Alamitos, CA (US); Scott David Eamer, Beverly Hills, CA (US)

(73) Assignee: Sscor, Inc., Sun Valley, CA (US)

( * ) Notice: Subject to any disclaimer, the term of this patent is extended or adjusted under 35 U.S.C. 154(b) by 436 days.

(21) Appl. No.: 12/113,896

(22) Filed: May 1, 2008

(65) Prior Publication Data
US 2008/0275460 A1 Nov. 6, 2008

Related U.S. Application Data

(60) Provisional application No. 60/927,675, filed on May 4, 2007.

(51) Int. Cl.
*A61M 1/00* (2006.01)
(52) U.S. Cl. ............................................. 604/35; 604/19
(58) Field of Classification Search ............... 604/19, 604/32–35, 119, 540, 902, 36, 264, 272, 604/317; 433/19, 31, 91
See application file for complete search history.

(56) References Cited

U.S. PATENT DOCUMENTS

| | | | |
|---|---|---|---|
| 2,482,116 A | 9/1949 | Lanahan | |
| 2,555,493 A | 6/1951 | Kirschbaum | |
| 3,090,122 A | 5/1963 | Erickson | |
| 3,768,477 A * | 10/1973 | Anders et al. | 433/91 |
| 3,804,089 A | 4/1974 | Bridgman | |
| 3,955,579 A | 5/1976 | Bridgman | |
| 3,963,028 A | 6/1976 | Cooley et al. | |
| 4,959,049 A | 9/1990 | Smirmaul | |
| 5,013,300 A | 5/1991 | Williams | |
| 5,295,980 A | 3/1994 | Ersek | |
| 5,578,006 A | 11/1996 | Schon | |
| 5,817,050 A | 10/1998 | Klein | |
| 5,899,884 A * | 5/1999 | Cover et al. | 604/119 |
| 6,979,318 B1 | 12/2005 | McDonald et al. | |
| 2004/0210114 A1* | 10/2004 | Simon | 600/185 |
| 2006/0217657 A1* | 9/2006 | Yacowitz | 604/35 |
| 2006/0276774 A1 | 12/2006 | Mori | |

FOREIGN PATENT DOCUMENTS

| | | |
|---|---|---|
| DE | 210609 | 6/1984 |
| DE | 202005009717 | 12/2006 |
| SU | 825093 | 4/1981 |

* cited by examiner

*Primary Examiner* — Christopher D Koharski
(74) *Attorney, Agent, or Firm* — Connolly Bove Lodge & Hutz LLP; Billy A. Robbins

(57) ABSTRACT

A suction catheter having an elongated flexible hollow member and a spoon-shaped distal end designated to assist manual removal of large airway occluding particles from the oropharynx and mouth opening to near the epiglottis of a patient by an emergency caregiver. The tip of the spoon-shaped distal end defines an ovular orifice of sufficient size to remove both viscous and non-viscous matter including matter from the airway of the patient for conveyance through the hollow member. The catheter includes a flexible stylet member therein to permit bending of the catheter and causing it to retain its bent shape with the proximal end thereof away from the patient. An opening is provided in the catheter and communicates with internal airway for use in controlling the amount of suction provided by the connection of the proximal end of the catheter to a vacuum source.

5 Claims, 4 Drawing Sheets

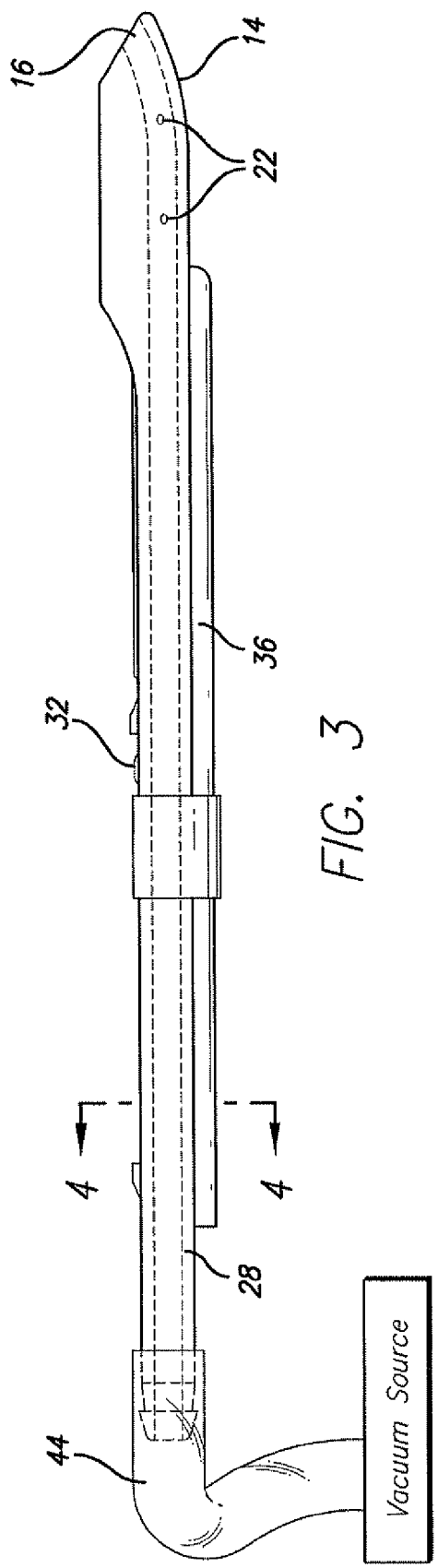
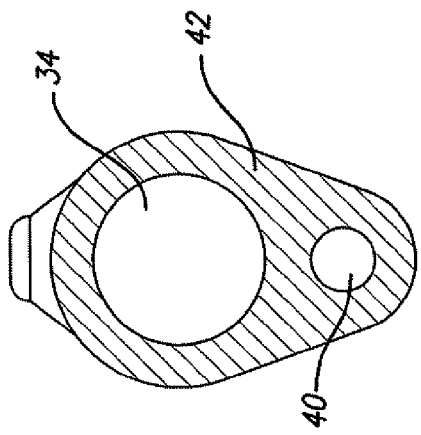
FIG. 3
FIG. 4

AIRWAY SUCTION SPOON

RELATED APPLICATIONS

This invention relates to Provisional Patent Application No. 60/927,675 filed May 4, 2007 and claims the benefit of the filing date thereof.

FIELD OF THE INVENTION

This invention relates to a suction catheter and more particularly to an instrument for use by a medical caregiver which is structured to be able to remove large airway occluding particles from the oropharynx and mouth of a patient while at the same time providing suction to remove viscous/non-viscous fluids from the airway of a human patient.

BACKGROUND OF THE INVENTION

It is well known that in an emergency situation involving human beings such, for example, as automobile accidents or other traumatic medical events, the airways of human beings can become occluded as a result of vomiting or an influx of bodily fluids which can deposit large particulate matter into the patient's airway. Paramedics and hospital technicians (caregivers) must clear the patient's airway of the fluids and/or solids in these emergency situations. If such is not done the patient will be asphyxiated because the airway is blocked preventing oxygen from entering the lungs.

To clear the airway of the fluids or solids in these emergency situations it is common to utilize a catheter typically in the form of an elongated hollow tube which is inserted into the patient's mouth and throat to withdraw the undesired materials. However, the catheters currently in use are incapable of removing the large airway occluding particles. As a result the caregiver first attempts to remove the large airway occluding particles manually, for example, by positioning his/her fingers into the mouth and oropharynx to withdraw these large particles. Such activity is undesirable because the patient may spasm causing injury to the fingers of the caregiver or alternatively the fingers may inject bacteria or other undesirable foreign elements into the mouth of the patient. These techniques thus meet with less than optimal results. Mortality of patients who aspirate gastric contents (vomit) can approach 75% or more due to the destructive effects on pulmonary tissue, infections, atelectasis and obstructive hypoxia.

The present invention was made with these effects and mitigation directly addressed. This device is designed to facilitate rapid decontamination and evacuation of the super-epiglottic oropharyngeal, buccal regions of the airway by virtue of its shape, mechanical function and integrated large bore suction. The caregiver can use the device to first reach deeply into the oropharynx with simultaneous suctioning or without suctioning and scoop out undesired airway occluding matter and if desired with simultaneous suctioning. The spoon like shape of the device allows for either shallow or deep displacement and suctioning of the upper airway thereby facilitating more complete and effective airway clearance.

The instrument of the present invention is specially suited for the removal of large airway-occluding particles and fluids from the oropharynx from the mouth opening to near the epiglottis. The device is a thickened spoon like apparatus with incorporated suction tubing and an ovular fenestration/orifice at the spoon's tip to facilitate the removal of emesis (vomitus), large particulate matter, both viscous/non-viscous from the airway of a patient. The ovular fenestration/orifice at the device's tip is larger and designed as a collector for the smaller incorporated suction orifice within it. The instrument is to be attached to a remote suction device of types well-known to the art through the use of a reducing adapter. When compared to other airway suction devices, this device is particularly desired to assist in the manual/mechanical removal of undesirable material as well as with remote suction assistance. The distal one-third of this instrument's construction is spoon like in nature to facilitate compliance and therapeutic function within a human airway. The distal and ovular fenestration and incorporated suction tubing are of an especially large bore to facilitate the removal of large particulate matter and fluids of varying viscosities contaminating the airway. An orifice is also optional and installed in the lateral aspect to the device's handle to enable a user to defer suction from the tip if necessary. The device is optimally a one time use and disposable instrument but can also be constructed of a reusable autoclavable piece, if an acceptable material is used.

The catheter of the presentation invention is preferably constructed from molded plastic materials strong enough at the distal spoon shaped end to scoop chunks of material from the patient's mouth and oropharynx, yet along the length thereof displaced from the spoon-like end, flexible enough or pliable to be bent. In accordance with one feature of the present invention a stylet in the form of a pliable piece of aluminum or similar material may be carried by the elongated portion or handle area of the catheter. This will allow the catheter to be bent and held into position so the tip of the catheter can be placed in the oropharynx and the shaft of the catheter can then be placed at the side of the patient's mouth with the proximal portion of the catheter bent out of the caregiver's way. This will allow the catheter to continue to suction while the caregiver performs other operations.

SUMMARY OF THE INVENTION

A catheter for use by an emergency caregiver to remove large airway occluding particles and fluids from the pharynx and which includes a hollow elongated member having a spoon shaped distal end having tip defining orifices of a size to pass at least a portion of the occluding particles into the hollow interior thereof, a handle portion disposed on the elongated member displaced from the distal and means at the proximal end for attaching a vacuum source to the member for producing suction to cause said occluding particles and fluids to enter said hollow portion of said member.

BRIEF DESCRIPTION OF THE DRAWINGS

FIG. 3 is a side view thereof;

FIG. 4 is a sectional view taken about lines 4-4 of FIG. 2; and

DETAILED DESCRIPTION

Figure 1:
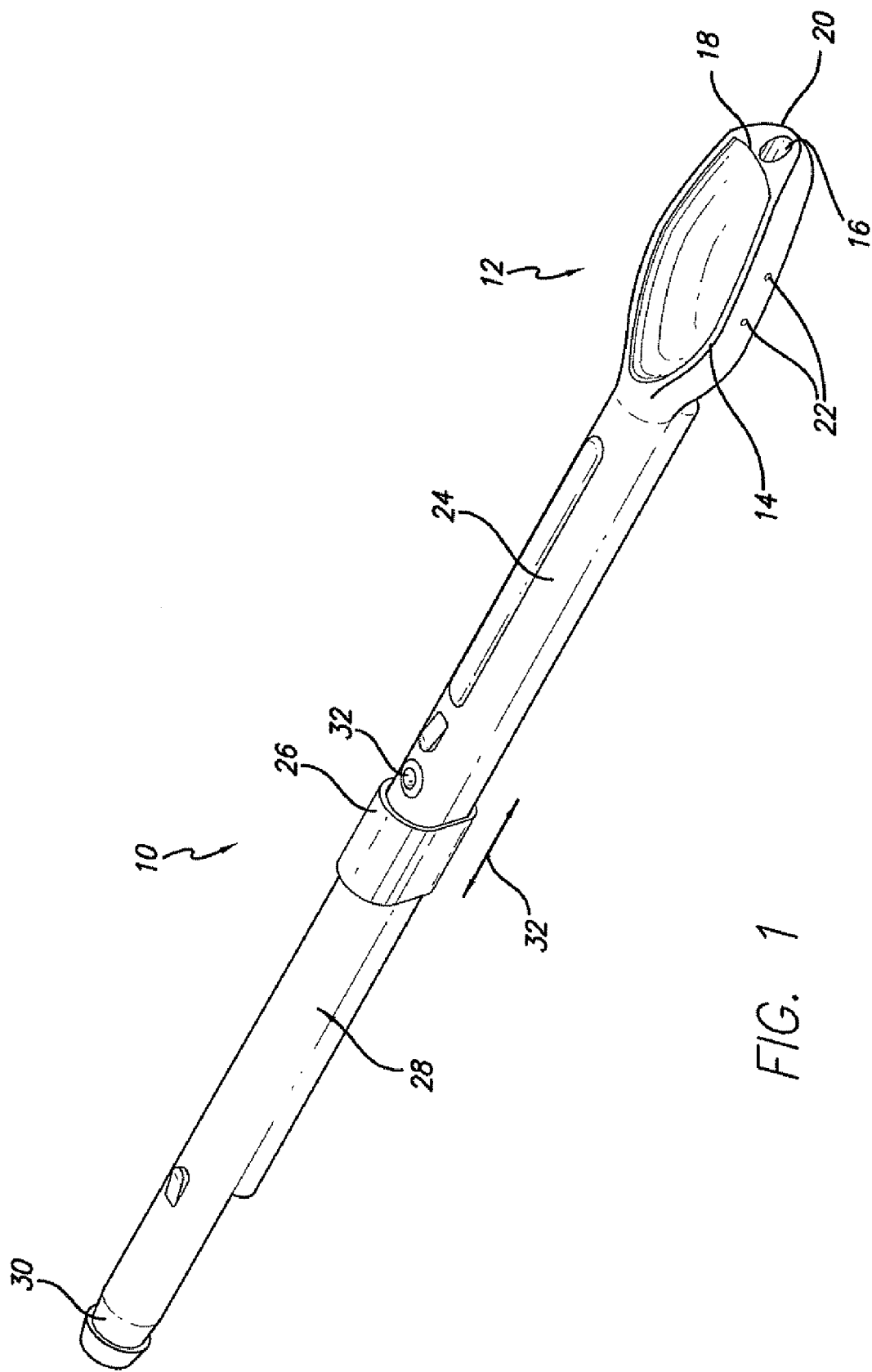
FIG. 1 is a perspective view of a catheter constructed in accordance with the principles of the present invention.

By reference now more particularly to FIG. 1, there is shown a suction catheter 10 constructed in accordance with the principles of the present invention. As is illustrated a distal end portion 12 of the suction catheter 10 is shaped like a spoon 14. At the very tip of the spoon there is provided an orifice 16 which is ovular in shape and has an upper portion 18 which is displaced from the tip 20. Additional, openings 22 are distributed about the periphery of the spoon-like portion 14 to provide additional suction for the passage of fluids in to the internal hollow portion of the catheter 10 as well as to prevent the catheter from adhering to the mucus or the lining of the pharynx. The spoon-like portion 14 and at least a portion of the elongated hollow section 24 of the catheter 10 is constructed of material which is strong enough that it is rigid so that the caregiver can grasp the elongated portion 24 and use the spoon to enter the mouth, pharynx and epiglottis of the patient to remove large chunks of occluding material from that area. The spoon-like member 14 is shaped to comply with the shape of the airway, tongue and oropharyngeal space in order to be positioned therein to remove the unwanted obstructive particles and fluids and to remain there to continuously remove fluids through the suction while the caregivers performing other operations during the emergency care.

The upper portion 28 of the handle is preferably formed of flexible material which will allow the elongated hollow member 24 to be bent. As will be more fully described and illustrated herein, the tubular hollow member 24 once bent, will retain its bent position so that the distal end 12 of the suction catheter can remain positioned in the oropharyngeal space and continuous suction may be applied to remove unwanted fluids while the caregiver is providing other treatment to the patient. The proximal end 30 of the catheter 10 would thus be out of the caregiver's way during this time. The catheter 10 is preferably molded polyvinylchloride plastic and may alternatively be made of urethane plastic material.

Also formed as a part of the catheter 10 is an opening 32 which may be utilized to control the suction in the catheter 10. The caregiver may place his/her thumb over the opening 32 and thus provide maximum suction to the suction catheter 10. If desired, there is provided a sleeve or slide 26 which can be manipulated as shown by the arrow 32 to cover the opening 32 thus freeing the caregiver to provide other services while maintaining maximum suction for the suction catheter 10. Stops 27 and 29 are provided to control the amount of movement of the slide 26.

Figure 2:
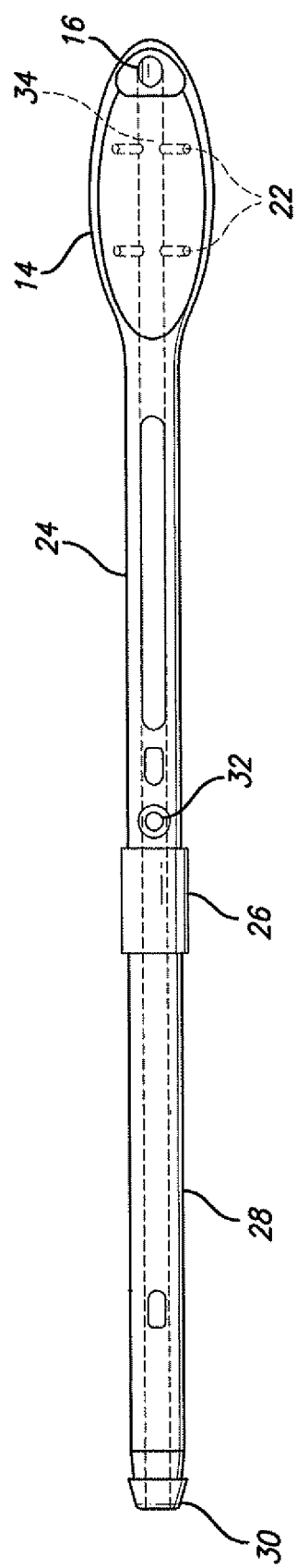
FIG. 2 is a top plain view thereof.

As is more clearly illustrated in FIG. 2, the spoon-like portion t4 has the opening 16 which has a relatively large diameter to assist in quickly suctioning the fluids and the larger semi-solid materials which could be lodged in the airway of the patient. These fluids and semi-sold particulates would pass through the opening 34 provided in the elongated hollow member forming the catheter 10. In accordance with one embodiment of the present invention, a sleeve 36 (FIG. 3) would be permanently attached to one side of the elongated hollow member 28. The sleeve would be designed to receive a stylet (FIG. 4) which may be molded in place or inserted therein. As is illustrated in FIGS. 1 and 3, the stylet is disposed intermediate the distal end 12 and the proximal end 30 and terminates at points displaced from the distal end 12 and the proximal end 30. The stylet would allow the catheter to then be bent in the region which is pliable or flexible and held in position by the stylet. This would allow the tip of the catheter with the opening 16 therein to be placed in the oropharynx of the patient with the shaft of the catheter bent and placed at the side of the patient's mouth and externally thereof with the proximal end 30 of the catheter bent out of the caregiver's way. This would then allow the catheter to continue to suction and remove unwanted fluids from the oropharynx of the patient while the caregiver performs other operations.

In accordance with another embodiment of the suction catheter constructed in accordance with the principles of the present invention, the stylet 40 may be a pliable strip of a metal material in situ molded into the plastic material 42 which forms the elongated hollow member 28 which provides the suction catheter 10 of the present invention. The strip of pliable or flexible metal material 40 would allow the catheter to be bent and held in position as above-described with regard to the stylet received within the sleeve 36.

As is shown in FIG. 3, the proximal end 30 of the elongated member 28 may be connected by appropriate tubing 44 to a vacuum source 46 which is well known in the industry to provide the appropriate suction to the suction catheter to allow it to function in the manner as above-described.

Figure 5:
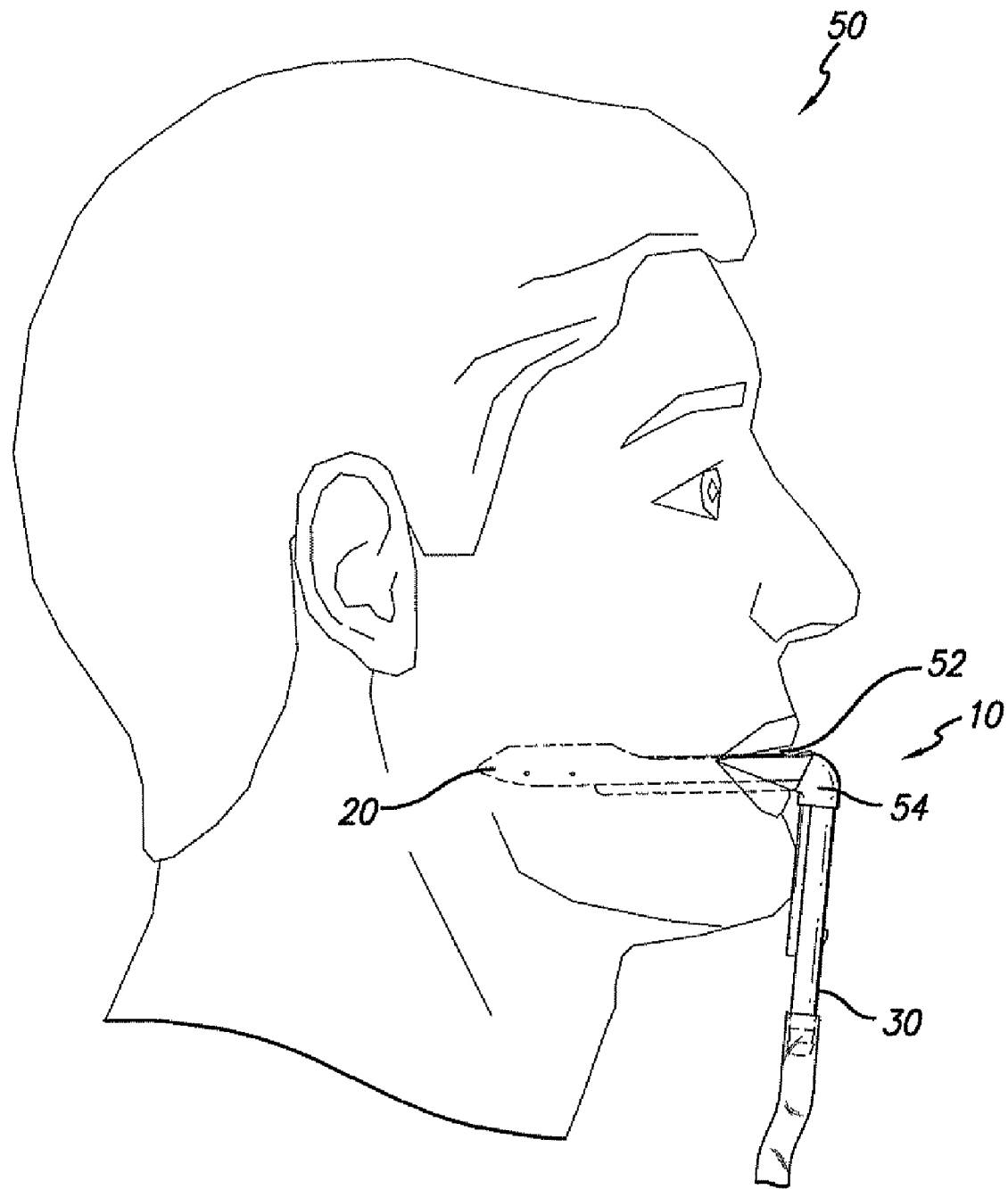
FIG. 5 is an illustration of the catheter of the present invention in place on a patient.

FIG. 5 illustrates a patient 50 with the catheter 10 of the present invention in place. The catheter 10 has been inserted into the mouth 52 of the patient and has been positioned so that the tip 20 thereof is positioned in the oropharnyx of the patient so that it can remove the particles and fluids as above-described. As is shown an elongated member is bent about the position 54 so that the proximal end 30 of the catheter 10 is disposed downwardly and adjacent the neck of the patient 50. In this manner, the catheter 10 continues to function while the caregiver provides additional operations and procedures upon the patient 50.

There has thus been described a suction catheter which is specifically designed to decrease mortality of airway comprised patients through its efficacy in removing quantities of large particulate matter and viscous and non-viscous fluid matter from the mouth and oropharnyx, super epiglottic regions of the airway.

What is claimed is:

1. A catheter having a proximal end a distal end for use by a medical care provider to remove large airway occluding particles and fluids from the pharynx of a human being comprising:
   a. a hollow elongated member having a spoon shaped member at said distal end, said spoon shaped member having a tip defining an orifice of sufficient size to pass at least portions of said large occluding particles into the hollow interior thereof, said spoon shaped member being configured to comply with the shape of the airway, tongue, and orpharyngeal space of a patient to permit deep or shallow placement thereof;
   b. said spoon shaped member at said distal end and a portion of the elongated hollow member adjacent thereto being rigid and can be used by a caregiver to directly remove said occluding particles from the mouth, pharynx and epiglottis of a human being;
   c. a portion of said hollow elongated member between said rigid portion thereof and said proximal end being flexible;
   d. a stylet integral with said elongated member and disposed intermediate said proximal and distal ends and terminates at points displaced from said distal and proximal ends in said flexible portion thereof for retaining said elongated member in a predetermined position after it has been bent;
   e. a handle portion disposed on said elongated member from said distal end;
   f. means at said proximal end for attaching a vacuum source to said member for producing suction to cause said occluding particles and fluids to enter said hollow portion of said elongated member.

2. A catheter as defined by claim 1 wherein said stylet is in situ molded into said elongated member.

3. A catheter ad defined in claim 2 wherein said stylet is an elongated pliable aluminum or similar material member extending along said flexible portion of said elongated member intermediate said proximal and distal ends.

4. A catheter as defined in claim 1 which further defines an orifice in said handle portion for controlling the application of suction.

5. A catheter as defined in claim 4 which further includes a member on said handle adjacent said orifice and movable between first and second positions to cover and uncover said orifice respectively.

* * * * *